(12) United States Patent
Weiss et al.

(10) Patent No.: US 10,662,130 B2
(45) Date of Patent: May 26, 2020

(54) PROCESS FOR GENERATION OF OLEFINS

(71) Applicant: ExxonMobil Research and Engineering Company, Annandale, NJ (US)

(72) Inventors: Brian M. Weiss, Bridgewater, NJ (US); ChangMin Chun, Annandale, NJ (US); Dhaval A. Bhandari, East Brunswick, NJ (US); Federico Barrai, Houston, TX (US); Sophie Liu, Hampton, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/101,790

(22) Filed: Aug. 13, 2018

(65) Prior Publication Data
US 2019/0055178 A1 Feb. 21, 2019

Related U.S. Application Data

(60) Provisional application No. 62/545,668, filed on Aug. 15, 2017.

(51) Int. Cl.
*C07C 5/48* (2006.01)

(52) U.S. Cl.
CPC .......... *C07C 5/48* (2013.01); *C07C 2521/06* (2013.01); *C07C 2521/08* (2013.01); *C07C 2523/04* (2013.01); *C07C 2523/14* (2013.01); *C07C 2523/30* (2013.01); *C07C 2523/34* (2013.01)

(58) Field of Classification Search
CPC ... C07C 5/48; C07C 2521/06; C07C 2521/08; C07C 2523/04; C07C 2523/14; C07C 2523/30; C07C 2523/34
See application file for complete search history.

(56) References Cited

U.S. PATENT DOCUMENTS

| 3,789,017 | A | * | 1/1974 | Walker | B01J 23/835 502/213 |
|---|---|---|---|---|---|
| 4,737,595 | A | | 4/1988 | Jones et al. | |
| 4,861,936 | A | | 8/1989 | Sofranko et al. | |
| 5,254,781 | A | * | 10/1993 | Calamur | B01J 8/009 585/500 |
| 7,622,623 | B2 | | 11/2009 | Fridman et al. | |
| 8,754,276 | B2 | | 6/2014 | Buchanan et al. | |

(Continued)

FOREIGN PATENT DOCUMENTS

WO 2015031366 A1 3/2015

OTHER PUBLICATIONS

The International Search Report and Written Opinion of PCT/US2018/046600 dated Feb. 11, 2019.

(Continued)

*Primary Examiner* — Ali Z Fadhel
(74) *Attorney, Agent, or Firm* — Kristina M. Okafor; Priya G. Prasad

(57) ABSTRACT

This disclosure relates to processes, compositions, and systems useful for the oxydehydrogenation of alkanes to form olefins (e.g., for the conversion of ethane to ethylene). The processes use an oxygen transfer agent and may be carried out in any suitable reactor, including a reverse flow reactor, a circulating fluid bed reactor, or a cyclic co-flow reactor.

22 Claims, 1 Drawing Sheet

(56) References Cited

U.S. PATENT DOCUMENTS

| | | | |
|---|---|---|---|
| 9,353,023 B2 | 5/2016 | Henao et al. | |
| 9,394,214 B2 | 7/2016 | Henao et al. | |
| 9,399,605 B2 | 7/2016 | Henao et al. | |
| 2013/0125462 A1 | 5/2013 | Greiner et al. | |
| 2014/0194663 A1* | 7/2014 | Butler | C07C 2/82 585/652 |
| 2015/0065769 A1* | 3/2015 | Henao | C07C 2/84 585/322 |
| 2015/0259265 A1 | 9/2015 | Fridman et al. | |
| 2017/0313637 A1* | 11/2017 | Sofranko | B01J 37/04 |
| 2018/0185806 A1 | 7/2018 | Sofranko | |
| 2018/0207599 A1 | 7/2018 | Metcalfe | |

OTHER PUBLICATIONS

Grubert et al., "Fundamental insights into the oxidative dehydrogenation of ethane to ethylene over catalytic materials discovered by an evolutionary approach", Catalysis Today, 81, 2003, 337-345.

Lomonsov et al., "Conjugation effects during ethane oxidation under the conditions of oxidative condensation of methane", XP002787323, retrieved from STN Database accession No. 2015:452394 abstract.

Arjmand et al., "$Ca_xLa_{1-x}Mn_{1-y}M_yO_{3-\delta}$ (M=Mg, Ti, Fe, or Cu) as Oxygen Carriers for Chemical-Looping with Oxygen Uncoupling (CLOU)", Energy & Fuels, 2013, 27, pp. 4097-4107.

Imanieh et al., "Novel Perovskite Ceramics for Chemical Looping Combustion Application", J. CO2 Utilization, 2016, 13, pp. 95-104.

Liu et al., "Influence of transition metal electronegativity on the oxygen storage capacity of perovskite oxides", Chem. Commun., 2016, 52, pp. 10369-10372.

Neal et al., "Oxidative Dehydrogenation of Ethane: A Chemical Looping Approach", Energy Technology, 2016. 4. pp. 1200-1208.

Yusuf et al., "Effect of Promoters on Manganese-Containing Mixed Metal Oxides for Oxidative Dehydrogenation of Ethan via a Cyclic Redox Scheme", ACS Catal., 2017, 7, pp. 5163-5173.

\* cited by examiner

PROCESS FOR GENERATION OF OLEFINS

CROSS-REFERENCE TO RELATED APPLICATIONS

This application claims priority to U.S. Provisional Application Ser. No. 62/545,668 filed Aug. 15, 2017, which is herein incorporated by reference in its entirety.

FIELD

Disclosed are reactors and materials useful in conducting dehydrogenation reactions in the absence of fuel combustion processes.

BACKGROUND

Ethylene and propylene are important building blocks for the petrochemical industry, and find use for production of polymers such as polyethylene, polypropylene, polystyrene and many others. Additionally, ethylene and propylene are used in the production of many other chemicals of commercial interest.

While a number of chemical processes are known for forming ethylene and propylene, the most commonly used process is thermal dehydrogenation of gaseous hydrocarbons or high-temperature steam cracking of light liquid components derived from processing of crude oil and natural gas condensate (e.g. ethane). In this process, gases such as ethane and propane are exposed to very high temperature conditions, resulting in the stripping of a hydrogen atom from each of two adjacent carbon atoms, forming the corresponding olefin. However, the process is very endothermic, and a great deal of energy must be generated to elevate the temperature of both the hydrocarbon and the reactor to a level sufficient to conduct the dehydrogenation.

Another method of dehydrogenation of hydrocarbons which has been proposed is oxidative dehydrogenation (ODH), in which an oxygen transfer agent (OTA) or oxidation catalyst is contacted with, for example, ethane under moderate temperature conditions, and one hydrogen from each carbon combines with an oxygen atom of the oxygen transfer agent or catalyst, to provide ethylene and water as the main products. An advantage of ODH is that less $H_2$ and $CH_4$ are formed during the reaction as compared to the amounts of those byproducts produced during thermal dehydrogenation processes. One disadvantage of the ODH reaction is that carbon monoxide (CO) and carbon dioxide ($CO_2$) are formed as low-value byproducts. A further disadvantage of ODH reactions is that nitrogen must be separated from either the feed air or the reactor product. Nitrogen separation from oxygen or light olefins by distillation is expensive because of the low boiling points of these species.

Chemical looping (CL) is a dynamic process in which a material, e.g., a metal oxide (which acts as an oxygen transfer agent or OTA) is used to provide an element such as oxygen for a reaction during which the material itself undergoes reduction. The reduced oxide or metal is then reoxidized in either a second reactor or in a second step if a fixed bed is used. The result is that a CL process physically (or temporally) separates an overall process into its separate oxidation and reduction steps through the use of a solid phase material capable of itself undergoing oxidation and reduction. CL has previously been applied to energy conversion, reforming, and water-gas shift processes. Importantly, the oxidizing and reducing streams fed to a CL process are never mixed with each other, and thus, an 'unmixed' reaction is performed.

The CL approach enables an ODH reactor that overcomes the challenge of nitrogen separation by distillation. In one form, at least two fixed bed reactors are used, each having a bed of OTA, at least a first reactor having the OTA in the oxidized form and at least a second reactor having the OTA in a reduced form. The ODH is conducted in the first reactor having the oxidized OTA bed, while the reduced OTA bed in the second reactor is regenerated with an oxygen-containing gas. Once the OTA in the first reactor is exhausted, the ODH reaction is switched to the second reactor and the first is subjected to regeneration/oxidation. The reactors are heat balanced such that the heat released by oxidizing the OTA supplies the energy needed for the process. In some cases, an extra source of energy is used to heat the feeds to the reactor, which adds cost and undesirable emissions.

Other reactors suggested for the process include moving bed reactors, such as fluidized bed reactors, which are quite expensive and complex in operation. A disadvantage of fixed and moving bed reactors is that they have limited control over the gas temperature, which is important for reactions. In both cases, a cooler hydrocarbon feed must contact a hot OTA to initiate the reaction. Therefore, the hydrocarbon may contact the OTA before thermal cracking reactions occur, which may affect and even depress reaction yield. The flows of regeneration and hydrocarbon gases are in the same direction, meaning the effluents exit the reactor at about the maximum temperature of the vapors in the reactor. This design increases the heat demand of the process and the capital employed for heat exchange. In addition, it is challenging to design a fast quench system for thermal reactions in such reactors, in part because the heat exchanger is typically located outside the reactor. A fast quench is typically needed to achieve high yields in such reactions. Furthermore, the fast quench is typically achieved by transferring heat from the olefin product to boil water in a heat exchanger after the reactor, which requires extra energy to heat up and boil water. It would be advantageous to find a suitable flow-through, fixed bed reactor with which to conduct chemical looping ODH, and effective OTA materials for such use.

Some materials suggested for use as OTA materials include Mn/B/MgO, Li/Mn/B/MgO, P/W/Li/Mn/B/MgO, and Na/B/Mn/Mg, and Mn/Na/P/$SiO_2$. However, these materials are not optimum as OTA materials for ODH reactions because they may convert hydrocarbons to products comprising an undesirably high yield of $CO_2$.

Some other materials suggested for the OTA include $Ca_xLa_{1-x}Mn_{1-y}M_yO_{3-n}$ wherein M is an element selected from the group consisting of Mg, Ti, Fe, and Cu. Another material includes $CaMnO_3$ doped with La, Fe, Sr, or Zr. These materials converted hydrocarbons to a product comprising an undesirably high yield of $CO_2$.

SUMMARY

Disclosed herein is a process for converting a $C_1$ to $C_6$ alkane to a $C_2$ to $C_6$ olefin. The process generally comprises passing an oxygen-containing gas in a first direction through a reverse flow reactor (RFR); contacting the oxygen-containing gas with an oxygen transfer agent to heat the reactor; terminating the oxygen-containing gas flow; passing a $C_1$ to $C_6$ alkane stream through the reactor in a second direction and past said oxygen transfer agent; reacting oxygen from the oxygen transfer agent with the $C_1$ to $C_6$ alkane under conditions sufficient to form $C_2$ to $C_6$ olefin and steam; and withdrawing an effluent comprising the $C_2$ to $C_6$ olefin from the reactor.

Also disclosed herein is an additional process for converting a $C_1$ to $C_6$ alkane to a $C_2$ to $C_6$ olefin. The process generally comprises adding an oxygen-containing gas to a reactor; contacting the oxygen-containing gas with an oxygen transfer agent comprising tin and/or manganese, and at least one material selected from the group consisting of aluminum, cobalt, zirconium, yttrium, cerium, lanthanum, sodium, tungsten, and the oxides thereof to heat the reactor; terminating the oxygen-containing gas flow; adding a $C_1$ to $C_6$ alkane stream to the reactor; reacting the oxygen from the oxygen transfer agent with the $C_1$ to $C_6$ alkane under conditions sufficient to form $C_2$ to $C_6$ olefin and steam; withdrawing an effluent comprising the $C_2$ to $C_6$ olefin from the reactor.

In embodiments of the invention, the oxygen transfer agent comprises tin, cobalt, and optionally zirconium.

In embodiments of the invention, the oxygen transfer agent comprises manganese, sodium, and tungsten.

In embodiments of the invention, the process is carried out in a reverse flow reactor, a circulating fluid bed reactor, or a cyclic co-flow reactor.

BRIEF DESCRIPTION OF THE DRAWINGS

The present disclosure is amenable to various modifications and alternative forms, specific exemplary implementations thereof have been shown in the drawings and are herein described in detail. It should be understood, however, that the description herein of specific exemplary implementations is not intended to limit the disclosure to the particular forms disclosed herein.

DETAILED DESCRIPTION

Figure 1A:
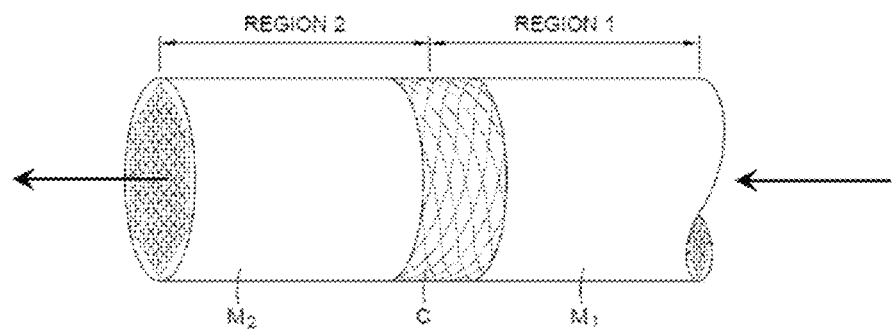
FIG. 1A is an example of a flow-through reactor, which includes a thermal mass and at least one oxygen storage material.

There is an increased interest in developing more energy-efficient methods of dehydrogenating alkanes to form olefins. The present disclosure is directed towards a chemical looping method which requires little, if any, heat from external sources to conduct otherwise endothermic reactions.

Definitions

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of the present invention described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data. All numerical values within the detailed description and the claims herein are modified by "about" or "approximately" the indicated value, and take into account experimental error and variations that would be expected by a person having ordinary skill in the art.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements). As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "$C_n$" hydrocarbon wherein n is a positive integer, e.g., 1, 2, 3, 4, or 5, means hydrocarbon having n carbon atom(s) per molecule.

The term "$C_{n+}$" hydrocarbon wherein n is a positive integer, e.g., 1, 2, 3, 4, or 5, means hydrocarbon having at least n carbon atom(s) per molecule.

The term "$C_{n-}$" hydrocarbon wherein n is a positive integer, e.g., 1, 2, 3, 4, or 5, means hydrocarbon having no more than n number of carbon atom(s) per molecule.

The term "alkane" means substantially saturated compounds containing hydrogen and carbon only, e.g., those containing ≤1% (molar basis) of unsaturated carbon atoms. The term alkane encompasses $C_2$ to $C_6$ linear, iso, and cyclo alkanes.

The term "unsaturated" means a $C_n$ hydrocarbon containing at least one carbon atom directly bound to another carbon atom by a double or triple bond.

The term "oxidant" means any oxygen-bearing material which, under the conditions in the reaction zone, yields oxygen for transfer to the oxygen storage material, for storage with and subsequent release from the oxygen storage material to the oxidative coupling and/or oxydehydrogenation. While not wishing to be limited to theory, molecular oxygen atoms may be provided as a reactive gas in a gaseous zone and/or atomic oxygen may be provided from a catalyst surface as, for instance, reacted, sorbed forms.

The term "oxydehydrogenation" means oxygen-assisted dehydrogenation of an alkane, particularly a $C_{2+}$ alkane, to produce an equivalent alkene and water.

The term "residence time" means the average time duration for non-reacting (non-converting by oxidative coupling) molecules (such as He, $N_2$, Ar) having a molecular weight in the range of 4 to 40 to traverse the reactor or a defined zone within the reactor, such as a reaction zone of a oxidative coupling reactor.

The term "reaction stage" or "reactor stage" means at least one flow-through reactor, optionally including means for conducting one or more feeds thereto and/or one or more products away therefrom.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" or "reactor zone" is a volume within the reactor for conducting at least one of oxidative coupling, oxydehydrogenation and dehydrocyclization. Similarly, a "quench zone" or "quenching zone" is a location within the reactor for transferring heat from products of the catalytic hydrocarbon conversion, such as $C_{2+}$ olefin.

The term "flow-through reactor" refers to a reactor design in which feeds and/or reaction mixtures can flow through the reactor, e.g., where oxidant feeds, hydrocarbon reactant feeds, and/or reaction mixtures coming into contact with the first and/or second hydrocarbon conversion catalyst and/or oxygen storage material as the feeds and/or reaction mixtures flow through the reactor.

One form of flow through, fixed bed reactor that can be used to conduct endothermic, chemical looping reactions is a reverse flow reactor (RFR). Such reactors and systems are disclosed in U.S. Pat. Nos. 9,394,214 and 9,399,605, both of which are incorporated herein by reference in their entireties. These patents disclose the use of oxygen storage media (oxygen transfer agents) in RFRs to oxidatively couple methane molecules to form longer-chained hydrocarbons, such as $C_{2+}$ olefins and the like. However, the reactions disclosed in these patents are unrelated to the presently disclosed process, wherein an alkane is oxydehydrogenated to form an olefin. Additionally, a typical fuel-air combustion scheme to reheat reverse flow reactors is disclosed in these patents, which is not necessary in the presently disclosed process.

The presently disclosed process incorporates reactors, systems, and reaction processes for contacting hydrocarbon reactant in the presence of oxygen stored and released from an OTA. The OTA can be one having thermal mass, or alternatively or in addition, can be located proximate to, on, or within a thermal mass located in at least one region of the reactor. The heat in the reactor and the presence of the OTA result in the formation of olefin products along with steam, carbon monoxide, and/or carbon dioxide. While not wishing to be bound by any theory or model, it is believed that a part of the conversion process is a result of thermal or catalytic dehydrogenation of the hydrocarbons to olefins and hydrogen, followed by a subsequent step in which hydrogen or hydrocarbons react with oxygen from the OTA to form water, carbon monoxide, and carbon dioxide.

The reaction process according to the presently disclosed process is exemplified by the equation:

wherein MO is a metal oxide that can comprise one or more oxides of manganese or tin, and which can further comprise one or more of magnesium, calcium, strontium, aluminum, cobalt, zirconium, yttrium, cerium, lanthanum, silicon, titanium, sodium, or tungsten. The MO may further comprise a perovskite structure, which can further comprise Ca, Sr, Ba, La, Y, Ti, Zr, Cr, Mn, Fe, Co, Sn, Ce. The MO is characterized herein as the OTA.

Exothermic regeneration of the OTA during the regeneration step provides the heat necessary to conduct the subsequent endothermic reaction in the reaction step, thereby eliminating fuel-air based combustion systems and the accompanying generation of carbon oxides and coke, and simplifying reactor design significantly. The disclosed method has advantages over other reactor systems (e.g., circulating fluid beds) that could employ the described OTA, due to better thermal management and less agitation of the active material.

Oxygen storage and release for carrying out the hydrocarbon conversion is achieved by regenerating the OTA. In certain aspects, a thermal mass is utilized which comprises, consists essentially of, or consists of OTA. Oxygen is transferred from an oxidant to the OTA for storage within the OTA. Oxygen is typically transferred and stored as the oxidant is passed through the thermal mass region of the reactor. Oxygen can be transferred from the oxidant to the OTA for storage with the OTA in any form, e.g., as oxygen atoms, oxygen ions, or as a component of an oxygen-containing molecule (e.g., an oxygen precursor). Stored oxygen released from the OTA for reacting with the hydrocarbon reactant to produce the first reaction mixture can be in any form, e.g., as oxygen atoms, oxygen ions, or as a component of an oxygen-containing molecule (e.g., an oxygen precursor).

Storage of the oxygen causes the thermal mass to be heated. For example, storage of the oxygen can be accompanied by exothermic reaction with the thermal mass. Thus, the oxidant itself can be considered a heating fluid for heating the flow-through reactor. The regeneration step proceeds according to the equation:

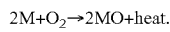

Presented herein is a process for converting a $C_1$ to $C_6$ alkane to a $C_2$ to $C_6$ olefin, comprising passing an oxygen-containing gas in a first direction through a reverse flow reactor (RFR); contacting the oxygen-containing gas with an oxygen transfer agent comprising a metal oxide to heat the reactor; terminating the oxygen-containing gas flow; optionally purging the oxygen-containing gas from the reactor with steam, inert gas, or vacuum purge; passing a $C_1$ to $C_6$ alkane stream through the reactor in a second direction and past the oxygen transfer agent; reacting oxygen from the oxygen transfer agent with the $C_1$ to $C_6$ alkane under conditions sufficient to form $C_2$ to $C_6$ olefin and steam; optionally purging the $C_1$ to $C_6$ alkane and olefin from the reactor with steam or inert gas; and withdrawing an effluent comprising the $C_2$ to $C_6$ olefin from the reactor.

FIG. 1A illustrates a flow-through reactor, for example a reverse-flow reactor having a first region (Region 1) and a second region (Region 2), with the first and second regions comprising thermal mass. Valves, for example poppet valves or another suitable type of valve, are used to regulate flows of all gases entering and exiting the reactor.

The process described herein, however, is not limited to being conducted in reverse flow reactors having two regions, and the FIG. 1A description is not intended to foreclose other configurations of thermal mass. For example, the thermal mass material may be coupled together as a continuous mass in a single region or more than one region or separate thermal masses may be coupled together, forming more than one region. As another example, the thermal mass can be a continuous mass of a ceramic material having an oxygen-storage functionality.

The terms first and second thermal mass segments are used for convenience in FIG. 1A to particularly describe the heating and cooling of the regions of the thermal mass as the oxygen transfer reaction progresses through the flow of the feeds and conversion products through the reactor. The reaction being carried out results in sorption and release of heat in a manner that is effective in the continuous conversion of alkanes in the hydrocarbon reactant feed to produce a reaction mixture comprising $C_2$ to $C_6$ olefin compositions.

The reactor in FIG. 1A includes a continuous thermal mass, which is represented as a first thermal mass segment M1 and a second thermal mass segment M2, with the thermal mass including a Reaction Zone C. The Reaction Zone C comprises at least one OTA, which can be further incorporated on or in either or both of the thermal mass segments M1 and M2. For example, all of the OTA can be incorporated in or on either thermal mass segment M1 or thermal mass segment M2 or a portion of the OTA can be incorporated in or on both thermal mass segment M1 and thermal mass segment M2. Advantageously, the OTA is incorporated primarily in Reaction Zone C.

Figure 1B:
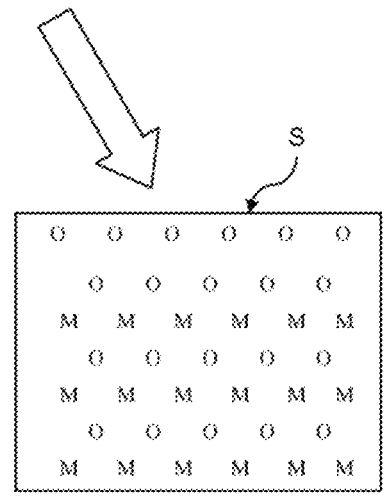
FIG. 1B is a simplified sectional enlargement of a reaction of the thermal mass, in which "M" refers to a metal center, representative of at least one oxygen storage material, and "O" refers to oxygen from an oxidant, which has been stored with the thermal mass.

FIG. 1B is a characterization of a cross-sectional enlargement of the Reaction Zone C. "M" of FIG. 1B refers to a metal center, representative of at least one OTA. "O" of FIG. 1B refers to an oxidant such as oxygen, which has been stored in the Reaction Zone C from a regeneration step in which heating fluid comprising an oxidant is flowed through the reactor.

As seen in FIG. 1B, oxygen from the oxidant can be stored in a portion of the thermal mass of the reaction zone containing OTA "M". As the oxidant is flowed through the reactor, at least a portion of the oxidant (i.e., oxygen) is stored with the OTA. The oxygen can migrate from the surface S of the thermal mass toward a more central region of the thermal mass, becoming more deeply embedded in the thermal mass. As flow of oxidant continues, the storage of oxygen can reach a maximum or saturation-type level.

As the hydrocarbon reactant (e.g., ethane) is flowed through the reactor, the stored oxygen is released and oxidatively dehydrogenates the alkane in the hydrocarbon reactant to produce a reaction mixture comprising a $C_{2+}$ olefin composition, with minimal amounts of carbon oxides, hydrogen and coke formed.

Operating pressures may include a pressure of at least atmospheric pressure (zero pressure, gauge), such as ≥4 pounds per square inch gauge (psig) (28 kilo Pascals gauge (kPag)), or ≥10 psig (69 kPag), or ≥36 psig (248 kPag), or ≥44 psig (303 kPag), or ≥103 psig (709 kPag), but may be ≤300 psig (2064 kPag), or ≤100 psig (689 kPag), or ≤30 psig (206 kPag).

Residence times in the reactor may be ≤10 seconds and even ≤5 seconds, or in the range of 0.01 seconds to 5 seconds, 0.5 seconds to 5 seconds, 0.1 seconds to 3 seconds, 0.1 seconds to 1 second, or 0.1 to 0.6 seconds. For a reverse-flow reactor, the process may operate at cycle times ≥0.5 second, such as in the range of 10 seconds to 240 seconds, in the range of 10 seconds to 120 seconds, in the range of 20 seconds to 60 seconds, or in the range of 20 seconds to 40 seconds. The term "cycle time" means the time from a first interval to the next first interval, including (i) intervening second, third, and/or fourth intervals and (ii) any dead-time between any pair of intervals.

Also, as may be appreciated, these different pressures and residence times may be utilized together to form different combinations depending on the specific configuration of equipment.

Figure 2:
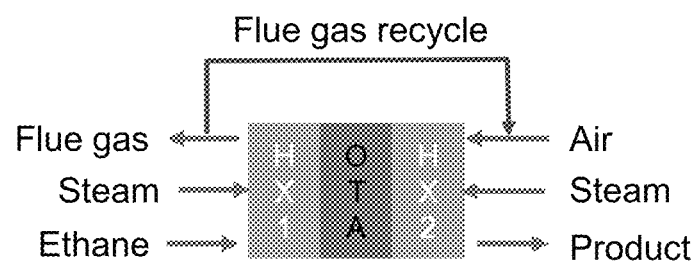
FIG. 2 is a schematic view of one advantageous configuration for the RFR used to conduct the presently disclosed process.

FIG. 2 is a schematic view of one advantageous configuration for the RFR used to conduct the presently disclosed process. A reverse flow reactor comprises the elements in FIG. 2: (1) In-flows of $C_2$-$C_6$ hydrocarbon, air, flue gas recycle, and steam; (2) Out-flows of flue gas and reaction product; (3) A section for heat exchange between flue gas and ethane (HX1); (4) A section comprising the oxygen transfer agent (OTA); and (5) A section for heat exchange between air and reaction product (HX2). The flows may be regulated by valves.

The reactor operation comprises alternating flow of streams comprising air and hydrocarbon. In some embodiments, steam or inert gas is flowed to purge air or hydrocarbon from the reactor between switches from regeneration flow and product formation flow. In other embodiments, the purge is accomplished by applying vacuum or a combination of vacuum, steam, or inert gas. In yet other embodiments, no purge is applied. The temperature of the effluents is controlled by the level of flue gas recycle and the size of the heat exchange sections. The product yield is controlled by the intrinsic OTA properties, the loading of OTA in the reactor, and the duration for which hydrocarbon is flowed to the reactor.

The OTAs useful in the presently disclosed process are metals/metal oxides, especially those comprising manganese/manganese oxide and/or tin/tin oxide. When used in a RFR, these OTAs enable very high yields of ethylene from hydrocarbon feeds, such as those comprising ethane, propane, butane, or naphtha. The OTA releases oxygen when contacted with hydrocarbons during a reaction step, leading to the formation of primarily ethylene, steam, and other olefins (endothermic reactions). The yields of carbon oxides, hydrogen, methane, and other alkanes are suppressed.

The regenerated OTA comprises oxides of one or more of manganese, tin, and magnesium and can further comprise oxides of one or more of aluminum, cobalt, zirconium, yttrium, cerium, lanthanum, sodium, and tungsten, and comprises less than 1 wt. % of lithium, sodium, and potassium. In one form, the composition comprises a cubic crystal lattice comprising magnesium and manganese. Advantageously, the composition comprises from about 1-2 moles of manganese, from about 6-7 moles of magnesium, and from about 0.5-2 moles of one or more of aluminum, zirconium, yttrium, cerium, or lanthanum.

The OTA can be packed in the reactor in the form of pellets, or can be washcoated on a ceramic monolith, such as a honeycomb monolith, which has at least one channel for establishing the specified flows of oxidant and hydrocarbon reactant. The OTA material may also be extruded in the form of such a monolith.

In another form, the oxygen transfer agent comprises a perovskite with the general formula $ABO_3$. Advantaged perovskite compositions comprise Cr, Mn, Fe, Co, Zr, Sn, or Ti in the B site and Ca, Sr, Ba, La, or Y in the A site.

For example, the OTA can be a perovskite of the general formula $ABO_3$, wherein the A- and/or B-sites are doped with metal cations to form a doped perovskite structure of the formula $A_xA'_yA''_zB_rB'_sO_{3-n}$. The A-site comprises La or Y with the number x between about 0.0 and about 0.5. The A'-site or A" site comprise elements selected from Ca, Sr, or Ba with the numbers y and z between 0.0 and 1.0. The B-site comprises Ti or Zr with the number r between 0.5 and 0.99. The B'-site comprises elements selected from the group consisting of Cr, Mn, Fe, Sn, or Co with the numbers and t between about 0.01 and about 0.5. The sum of the numbers x, y, and z is about 1.0 and the sum of the numbers r, s, and t is about 1.0. The number n is a number between 0.0 to about 0.5. In another form, the numbers x and s are about equal to each other.

Alternatively, the OTA is a perovskite of the general formula $ABO_3$, wherein the A- and/or B-sites are doped with metal cations to form a doped perovskite structure of the formula $A_xA'_{1-x}B_yB'_{1-y}O_{3-n}$, wherein A is an element selected from La or Y or combinations thereof; A' is an element selected from Sr, Ba or Ca or combinations thereof; B is element selected from Cr, Mn, Fe, Sn or Co or combinations thereof; and B' is an element selected from Ti or Zr or combinations thereof; x and y are numbers from about 0.01 to about 0.95, or from about 0.01 to about 0.5, and n is a number from about 0.0 to about 0.5. In one form, the ratio of the numbers x toy is between about 0.8 and about 1.5.

In some forms, the perovskite is one in which A is a combination of La and Y, and/or A' is a combination of at least two of Sr, Ba and Ca, and/or B is a combination of at least two of Cr, Mn, Fe, Sn, and Co, and/or B' is a combination of Ti and Zr.

Alternatively, the OTA can be a perovskite of the general formula $ABO_3$, wherein the A- and/or B-sites are doped with metal cations to form a doped perovskite structure of the formula $A_xA'_yA''_zB_rB'_sB'''_tO_{3-n}$. The A-site comprises La or Y with the number x between about 0.0 and about 0.5. The A'-site or A" site comprise elements selected from Ca, Sr, or Ba with the numbers y and z between about 0.0 and about 1.0. The B-site comprises Ti or Zr with the number r between about 0.5 and about 0.99. The B'-site and B"-site comprise elements selected from the group consisting of Cr, Mn, Fe, Sn, or Co with the number s and t between about 0.01 and about 0.5. The sum of the numbers x, y, and z is about 1.0 and the sum of the numbers r, s, and t is about 1.0. The number n is a number between about 0.0 to about 0.5. In another form, the number x is about equal to the sum of s and t. In one form, the ratio of the number x to the sum of the numbers s and t is between about 0.8 and about 1.5.

For example, the doped perovskite can be any of $La_{0.6}Sr_{0.2}Co_{0.2}Fe_{0.8}O_3$, $Ba_{0.5}Sr_{0.5}Co_{0.8}Fe_{0.2}O_3$, $La_{0.6}Sr_{0.4}Co_{0.8}Cr_{0.2}O_3$, $La_{0.6}Sr_{0.4}Co_{0.8}Mn_{0.2}O_3$, $La_{0.8}Sr_{0.2}FeO_3$, $Y_{0.1}Ba_{0.9}CoO_3$), $Ca_{0.8}La_{0.2}Zr_{0.8}Mn_{0.2}O_3$, $Ca_{0.4}Ba_{0.4}La_{0.2}Zr_{0.8}Mn_{0.2}O_3$, $Ca_{0.4}Ba_{0.4}La_{0.2}Zr_{0.8}Mn_{0.1}Fe_{0.1}O_3$, $Sr_{0.8}La_{0.2}Zr_{0.8}Mn_{0.2}O_3$, $Ba_{0.8}La_{0.2}Zr_{0.8}Mn_{0.2}O_3$, $Ca_{0.4}Sr_{0.4}La_{0.2}Zr_{0.8}Mn_{0.2}O_3$, $Ca_{0.8}La_{0.2}Zr_{0.8}Fe_{0.2}O_3$, $Ca_{0.8}La_{0.2}Zr_{0.8}Co_{0.2}O_3$, $Ca_{0.4}Ba_{0.4}La_{0.2}Zr_{0.8}Mn_{0.1}Co_{0.1}O_3$, $Ca_{0.8}La_{0.2}Ti_{0.8}Mn_{0.2}O_3$, $Ba_{0.8}La_{0.2}Ti_{0.8}Mn_{0.2}O_3$, $Ca_{0.8}Y_{0.2}Zr_{0.8}Mn_{0.2}O_3$, $Ca_{0.8}Y_{0.2}Ti_{0.8}Mn_{0.2}O_3$, or $Ca_{0.9}La_{0.1}Zr_{0.9}Mn_{0.1}O_3$, or $Ca_{0.9}Zr_{0.8}Sn_{0.2}O_3$.

In another form, the OTA comprises tin oxide and oxide of one or more of zirconium, cobalt, aluminum, titanium, or silicon. For example, the OTA may comprise tin oxide. Or for example, the OTA may comprise a mixture of cobalt and tin. The OTA may further comprise an oxide of chromium, manganese, iron, cobalt, nickel, cerium, lanthanum, yttrium, tungsten, sodium, potassium, or copper. For example, the OTA may comprise manganese and tungsten with sodium or potassium.

A relative flow of oxygen-containing gas and $C_2$-$C_6$ alkane are sufficient to achieve effluent temperatures below 400° C., or above 550° C. For example, the weight ratio of the flow rates of oxidizer gases (e.g., air, flue gas recycle, and steam) to ethane can be between 2.4 to 3.0. Low-temperature effluent is advantageous because it requires less capital to recover heat as steam. A heat exchanger can be used to recover heat from the reactor effluents, by boiling water to make steam. When the effluent is recovered at a higher temperature, it is possible to generate high pressure steam by flowing it though a boiler. The high pressure steam can be used to supply the purge steam to the reactor and for other purposes, such as generating work in a turbine expander.

Another aspect of the invention is the use of new compositions of matter for the OTA. To this end, OTAs comprising an active component (e.g., manganese oxide or tin oxide) dispersed among oxides comprising magnesium, aluminum, cobalt, zirconium, lanthanum, cerium, titanium, or yttrium are particularly advantageous. The material is essentially free of volatile components, such as alkali, comprising less than 1 wt % of lithium, sodium and potassium. The OTA can comprise from about 0.5-2.0 moles of manganese, from about 5.0-8.0 moles of magnesium, and from about 0.5-2.0 moles of one or more of aluminum, zirconium, yttrium, or lanthanum.

A method for making the new compositions of matter includes the co-precipitation method, comprising (1) dissolving all metal salts (e.g., salts of manganese, magnesium, tin, calcium, lanthanum, zirconium, and so on), in acidic solution with pH less than 7, (2) mixing said acidic solution with a basic solution with pH greater than about 7, (3) removing solids from the solution, and (4) heating the solids to a temperature above 500° C. The acidic solution can be in the form of nitrate, acetate, chloride, or glycolate, and the basic solution in the form of carbonate or hydroxide salts of ammonium, tetramethylammonium, lithium, sodium, or potassium. Advantageously, the solvent is water and the method is conducted at a temperature between about 10 to about 100° C.

As previously stated, the OTAs disclosed herein are not limited to use in a RFR. The reactor can be a reverse flow reactor, a circulating fluid bed reactor, or even a co-flow cyclic reactor. The process for converting a $C_1$ to $C_6$ alkane to a $C_2$ to $C_6$ olefin can comprise passing an oxygen-containing gas through a reactor; contacting the oxygen-containing gas with an oxygen transfer agent such as those described above to sorb the oxygen and heat the reactor; terminating the oxygen-containing gas flow; optionally purging the oxygen-containing gas from the reactor with steam, inert gas, or vacuum; passing a $C_1$ to $C_6$ alkane stream through the reactor past the oxygen transfer agent; desorbing oxygen from the oxygen transfer agent; reacting the desorbed oxygen with the $C_1$ to $C_6$ alkane under conditions sufficient to form $C_2$ to $C_6$ olefin and steam; and optionally purging the $C_1$ to $C_6$ alkane and olefin from the reactor with steam, inert gas, or vacuum.

EXAMPLES

OTA Examples

The description of the products formed in each of the OTA Examples below is provided for simplicity and does not imply the actual stoichiometric ratios of product formed. For example, $SnO_2/ZrO_2$ in OTA Example 1 indicates that $SnO_2$ and $ZrO_2$ were formed as a result of the reaction but should not be interpreted to suggest they were formed in a 1:1 stoichiometric ratio. The actual stoichiometric ratios of products formed can readily be calculated by one of ordinary skill in the art using the provided amounts of reactants.

OTA Example 1

$SnO_2/ZrO_2$ 6.17 g tin(IV) chloride pentahydrate and 14.89 g zirconium(IV) oxychloride octahydrate were added to water. The salt solution was added to 100 g of aqueous ammonium hydroxide solution to maintain the pH of the mixture at about 7. The precipitated solids were recovered by vacuum filtration and washed with deionized water. The sample was heated at 900° C. for 12 hr (3° C./min ramp).

OTA Example 2

$Mn_2O_3/SiO_2$ 10.0 g Manganese(II) acetate tetrahydrate was added to water at 80° C. to obtain 20 mL solution. The solution was thoroughly mixed with 20.0 g silica. The sample was heated at 120° C. for 6 hr, then at 600° C. for 6 hr (1° C./min ramp).

OTA Example 3

$Mn_2O_3/MnTiO_3$ 1.55 g Manganese(II) acetate tetrahydrate was added to 1 mL water at 80° C. The solution was thoroughly mixed with 5.0 g $MnTiO_3$. The sample was heated at 900° C. for 4 hr (3° C./min ramp).

OTA Example 4

$CO_3O_4/SnO_2/ZrO_2$ 3.085 g tin(IV) chloride pentahydrate, 17.72 g zirconium (IV) oxychloride octahydrate, and 1.14 g cobalt(II) chloride were dissolved in water. The solution was mixed with aqueous 25% tetramethylammonium hydroxide solution at constant pH of about 8. The solids were filtered from solution and heated at 110° C. for 16 hr. The material was then heated at 900° C. for 12 hr.

OTA Example 5

$CaMnO_3$ 9.0 g calcium nitrate and 14.0 g manganese(II) nitrate tetrahydrate were dissolved in water. The solution was mixed with 94.7 g of aqueous 16% tetramethylammonium hydroxide solution. The solids were filtered from solution and heated at 110° C. for 16 hr. The material was then heated at 200° C. for 2 hr and at 650° C. for 12 hr.

OTA Example 6

$Mn_2O_3/SiO_2$ 0.3 g $Mn_2O_3$ powder was mixed with 4 cm³ of quartz pellets.

OTA Example 7

$Mn_3O_4/Na_2WO_4/MnWO_4$ 0.82 g ammonium metatungstate hydrate, 0.49 g sodium tungstate dihydrate, and 0.67 g triethanolamine were dissolved in 0.67 g water. The solution was mixed thoroughly with 4.0 g $Mn_3O_4$ powder. The sample was heated at 80° C. for 16 hr and at 1100° C. for 8 hr.

Reaction Examples

Reaction Example 1

Thermal Cracking Reaction.

A flow of 0.2 sL/min ethane was contacted with quartz powder at 850° C. The residence time of the vapor in the heated zone was about 0.4 seconds. Table 1 shows the cumulative yield of products (in units of mole fraction in the dry product) with increasing duration that the ethane flow is contacted with the quartz. The table also shows the cumulative heat consumption by the process.

TABLE 1

| Reaction Example 1* | | | | | | |
|---|---|---|---|---|---|---|
| | Duration (seconds)** | | | | | |
| | 4 | 8 | 11 | 14 | 20 | 30 |
| Conversion | 67% | 66% | 66% | 66% | 66% | 66% |
| CO | 0.0% | 0.0% | 0.0% | 0.0% | 0.0% | 0.0% |
| CO2 | 0.0% | 0.0% | 0.0% | 0.0% | 0.0% | 0.0% |
| H2 | 34.8% | 36.1% | 36.6% | 36.9% | 37.5% | 38.1% |
| Methane | 6.7% | 6.4% | 6.2% | 6.1% | 6.1% | 6.0% |
| Ethane | 21.2% | 21.1% | 21.0% | 20.9% | 21% | 20.6% |
| Ethylene | 35.3% | 34.4% | 34.1% | 33.9% | 34% | 33.4% |
| C3+ | 2.0% | 2.0% | 2.0% | 1.9% | 1.9% | 1.9% |
| Heat consumption (kJ/g) | 2.78 | 2.78 | 2.79 | 2.79 | 2.8 | 2.82 |

*All yields reported as mole fraction in dry product
**Duration that ethane flow is exposed to reactor Reaction Example 2

$SnO_2/ZrO_2$

A flow of 0.2 L/min ethane was contacted with 1.0 gram of the OTA of OTA Example 1 at 850° C. The residence time of the vapor in the heated zone was about 0.4 seconds. Table 2 shows the cumulative yield of products (in units of mole fraction in the dry product) with increasing duration that the ethane flow is established on the OTA. The table also shows the cumulative heat consumption by the process, including the heat released by reoxidation of the OTA. It is notable that the ethylene concentration in the product is much higher than the case without the OTA. It is also notable that the $CO_2$ concentration and the heat release both decrease concomitantly as the duration of ethane contact increases. But the ethylene concentration in the product remains approximately constant between about 43% to 45% over the range in the Table.

TABLE 2

| Reaction Example 2* | | | | | | | |
|---|---|---|---|---|---|---|---|
| | Duration (seconds)** | | | | | | |
| | 4 | 7 | 10 | 13 | 18 | 23 | 33 |
| OTA/Ethane*** | 56 | 32 | 22 | 17 | 12 | 10 | 7 |
| Conversion | 69% | 68% | 67% | 67% | 66% | 66% | 66% |
| CO | 0.5% | 0.5% | 0.5% | 0.5% | 0.5% | 0.5% | 0.3% |
| CO2 | 9.0% | 5.9% | 4.5% | 3.6% | 2.8% | 2.3% | 1.6% |
| H2 | 5.3% | 7.6% | 9.0% | 9.9% | 10.9% | 11.9% | 15.2% |
| Methane | 10.4% | 9.9% | 9.5% | 9.2% | 8.9% | 8.7% | 8.2% |
| Ethane | 29.5% | 29.2% | 29.1% | 29.1% | 29% | 29.1% | 28.1% |
| Ethylene | 42.8% | 44.4% | 44.8% | 45.0% | 45% | 44.9% | 43.8% |
| C3+ | 2.5% | 2.7% | 2.7% | 2.7% | 2.7% | 2.6% | 2.6% |
| Heat release (kJ/g) | 2.4 | 1.9 | 1.6 | 1.4 | 1.2 | 1.1 | 0.7 |

*All yields reported as mole fraction in dry product
**Duration that ethane flow is exposed to OTA
***Ratio of the mass OTA to the cumulative mass of ethane flowed Reaction Example 3

$Mn_2O_3/SiO_2$

A flow of 0.2 sL/min ethane was contacted with 3.0 gram of the OTA of OTA Example 2 at 850° C. The residence time of the vapor in the heated zone was about 0.4 seconds. Table 3 shows the cumulative yield of products with increasing duration that the ethane flow is contacted with the OTA. The table also shows the cumulative heat consumption by the process, including the heat released by reoxidation of the OTA.

TABLE 3

| | Reaction Example 3* | | | | | | |
|---|---|---|---|---|---|---|---|
| | Duration (seconds)** | | | | | | |
| | 4 | 6 | 9 | 12 | 15 | 18 | 23 |
| OTA/Ethane*** | 56 | 37 | 25 | 19 | 15 | 12 | 10 |
| Conversion | 74% | 71% | 67% | 65% | 64% | 63% | 62% |
| CO | 7.6% | 5.7% | 3.8% | 2.7% | 2.0% | 1.6% | 1.2% |
| CO2 | 7.9% | 5.6% | 3.6% | 2.5% | 1.9% | 1.5% | 1.2% |
| H2 | 0.8% | 2.7% | 9.7% | 16.3% | 20.8% | 23.8% | 26.8% |
| Methane | 8.3% | 7.7% | 6.8% | 6.0% | 5.6% | 5.2% | 4.9% |
| Ethane | 25.9% | 28.0% | 28.9% | 28% | 27.9% | 27.6% | 27.5% |
| Ethylene | 47.6% | 48.2% | 45.3% | 42% | 39.9% | 38.3% | 36.7% |
| C3+ | 2.0% | 2.1% | 2.0% | 2.0% | 1.9% | 1.8% | 1.8% |
| Heat release (kJ/g) | 3.03 | 2.54 | 1.76 | 1.06 | 0.49 | 0.42 | 0.34 |

*All yields reported as mole fraction in dry product
**Duration that ethane flow is exposed to OTA
***Ratio of the mass OTA to the cumulative mass of ethane flowed Reaction Example 4

$Mn_3O_4/Na_2WO_4/MnWO_4$

A flow of 0.2 sL/min ethane was contacted with 0.8 gram of the OTA of OTA Example 7 at 850° C. The residence time of the vapor in the heated zone was about 0.4 seconds. Table 4 shows the cumulative yield of products with increasing duration that the ethane flow is contacted with the OTA. The table also shows the cumulative heat consumption by the process, including the heat released by reoxidation of the OTA.

TABLE 4

| | Reaction Example 4* | | | | | |
|---|---|---|---|---|---|---|
| | Duration (seconds)** | | | | | |
| | 5 | 7 | 9 | 12 | 15 | 18 |
| OTA/Ethane*** | 36 | 26 | 20 | 15 | 12 | 10 |
| Conversion | 71% | 72% | 72% | 72% | 73% | 73% |
| CO | 1.0% | 0.9% | 0.8% | 0.7% | 0.7% | 0.7% |
| CO2 | 1.5% | 1.4% | 1.3% | 1.1% | 1.0% | 0.9% |
| H2 | 16.2% | 17.1% | 17.8% | 18.9% | 20.1% | 21.2% |
| Methane | 10.3% | 10.2% | 10.0% | 9.8% | 9.6% | 9.4% |
| Ethane | 23.5% | 22.6% | 22.0% | 21% | 21.0% | 20.6% |
| Ethylene | 44.8% | 45.3% | 45.4% | 45% | 45.0% | 44.6% |
| C3+ | 2.6% | 2.7% | 2.7% | 2.6% | 2.6% | 2.6% |
| Heat release (kJ/g) | 0.71 | 0.65 | 0.56 | 0.44 | 0.31 | 0.20 |

*All yields reported as mole fraction in dry product
**Duration that ethane flow is exposed to OTA
***Ratio of the mass OTA to the cumulative mass of ethane flowed Reactor Examples Reactor Example 1

A circulating fluid bed system that yielded 200 T/hr ethylene circulated the OTA of OTA Example 2 between a reactor and regenerator at ratio of 10 T OTA per T ethane fed to the reactor. Inert diluent was also circulated so that the ratio of total circulated solids to ethane was 60 T/T. The residence time in the reactor was 0.4 seconds, allowing the same yield as reported in Table 2 for an OTA/ethane ratio of 10. The reactor was fed 410 T/hr ethane at 600° C. The reaction product exited at 850° C. The effluent product was quenched to 325° C. in a transfer line exchanger that boiled 500 T/hr water at 100 bar. An air compressor delivered air at 570 T/hr, 160° C. to a preheater that raised the temperature to 910° C. before flowing to the regenerator. The effluent flue gas exited the regenerator at 990° C. The energy in the flue gas was recovered in a heat exchanger, allowing an final flue gas temperature of 70° C. Excess heat demand was supplied by a fired heater. The heat balance is shown in Table 5. One can clearly see that a significant amount of fuel must be combusted in the fired heater to supply heat for the process. In addition, the air and ethane must be pre-heated to quite high temperatures to satisfy the heat balance.

TABLE 5

| Heat Balance for Reactor Example 1 | |
|---|---|
| | MW |
| Sources of heat demand | |
| Ethane preheat | 277 |
| Air preheat | 110 |
| Boiler water preheat | 99 |
| Boiler duty | 251 |
| Steam superheater duty | 196 |
| Reactor duty | 625 |
| Total demand | 1560 |
| Sources of Heat supply | |
| Product quench | 251 |
| Flue gas recovery | 135 |

TABLE 5-continued

Heat Balance for Reactor Example 1

|  | MW |
|---|---|
| Regenerator | 571 |
| Fired heater | 603 |
| Total supply | 1560 |

Reactor Example 2

A circulating fluid bed system that yielded 200 T/hr ethylene circulated the OTA of OTA Example 2 between a reactor and regenerator at ratio of 32 T OTA per T ethane fed to the reactor. Inert diluent was also circulated so that the ratio of total circulated solids to ethane was 60 T/T. The residence time in the reactor was 0.4 seconds, allowing the same yield as reported in Table 2 for an OTA/ethane ratio of 32. The reactor was fed 425 T/hr ethane at 585° C. The reaction product exited at 850° C. and comprised 200 T/hr ethylene. The effluent product was quenched to 325° C. in a transfer line exchanger that boiled 520 T/hr water at 100 bar. An air compressor delivered air at 770 T/hr, 160° C. to the regenerator. The effluent flue gas exited the regenerator at 980° C. The energy in the flue gas was recovered in a heat exchanger, allowing an final flue gas temperature of 70° C. Excess heat demand was supplied by a fired heater. The heat balance is shown in Table 6. Reactor Example 2 has an advantage over Reactor Example 1 because it uses less energy and does not require an air pre-heater. But, the yield of CO and $CO_2$ from Reactor Example 2 is much higher than from Reactor Example 1, which is undesirable.

TABLE 6

Heat Balance for Reactor Example 2

|  | MW |
|---|---|
| Sources of heat demand |  |
| Ethane preheat | 280 |
| Air preheat | 0 |
| Boiler water preheat | 104 |
| Boiler duty | 260 |
| Steam superheater duty | 206 |
| Reactor duty | 629 |
| Total demand | 1480 |
| Sources of Heat supply |  |
| Ethane quench | 260 |
| Flue gas recovery | 197 |
| Regenerator | 800 |
| Fired heater | 223 |
| Total supply | 1480 |

Reactor Example 3

A reverse flow reactor that yielded 200 T/hr ethylene comprised 57 T of the OTA of OTA Example 2 and 103 T of inert diluent. The reactor was fed 405 T/hr ethane at 180° C. for 33 seconds and the residence time was adjusted to 0.4 seconds, allowing the same yields as reported in Table 2 at 33 seconds on stream. The reaction product exited the reactor at 280° C. After the reaction, the reactor was purged. An air compressor fed 1240 T/hr air to the reactor at 160° C. in a reverse direction compared to the ethane flow. The effluent flue gas exited the reactor at 320° C. Energy was recovered by cooling the flue gas to 70° C. in a heat exchanger. The heat balance is shown in Table 7. One can clearly see that the reverse flow reactor enables improved operation at conditions at which the catalyst achieves the more favorable yields (i.e. lower CO and $CO_2$) versus the circulating fluid bed reactors. The reverse flow reactor eliminates the air preheater, steam boiler system, and fired heater. Moreover, the demand on the feed preheater and the flue gas recovery are much smaller.

TABLE 7

Heat Balance for Reactor Example 3

|  | MW |
|---|---|
| Sources of heat demand |  |
| Ethane preheat | 76 |
| Air preheat | 0 |
| Boiler water preheat | — |
| Boiler duty | — |
| Steam superheater duty | — |
| Reaction step | 539 |
| Total demand | 615 |
| Sources of Heat supply |  |
| Ethane quench | — |
| Flue gas recovery | 92 |
| Regeneration step | 523 |
| Fired heater | — |
| Total supply | 615 |

INDUSTRIAL APPLICABILITY

The systems and methods disclosed herein are applicable to the chemical industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A process for oxydehydrogenation of a $C_2$ to $C_6$ alkane to a $C_2$ to $C_6$ olefin, comprising:
passing an oxygen-containing gas in a first direction through a reverse flow reactor (RFR), the RFR comprising an oxygen transfer agent and a thermal mass;
contacting the oxygen-containing gas with the oxygen transfer agent to exothermically oxidize a metal comprised in the oxygen transfer agent and produce heat that is stored in the thermal mass of the reactor;
terminating the oxygen-containing gas flow;
passing a stream comprising $C_2$ to $C_6$ alkane through the reactor in a second direction and past said oxygen transfer agent;
oxidatively dehydrogenating the stream by reacting oxygen from the oxidized metal of the oxygen transfer agent with the $C_2$ to $C_6$ alkane to form $C_2$ to $C_6$ olefin and steam; and
withdrawing an effluent comprising the $C_2$ to $C_6$ olefin from the reactor,
wherein the oxygen transfer agent comprises manganese and tungsten.

2. The process of claim 1, further comprising purging the oxygen-containing gas from the reactor using steam, an inert gas, or a vacuum purge after the terminating step.

3. The process of claim 1, further comprising purging the $C_2$ to $C_6$ alkane and the $C_2$ to $C_6$ olefin from the reactor using steam, an inert gas, or a vacuum purge after the terminating step.

4. The process of claim 1, wherein a weight ratio of the relative flows of the oxygen-containing gas and the $C_2$ to $C_6$ alkane is between 2.4 and 3.0.

5. The process of claim 4, wherein the oxygen-containing gas comprises air, flue gas, steam, or combinations thereof.

6. The process of claim 1, further comprising recovering heat from the reactor effluent in a heat exchanger to boil water to make steam or to heat water or steam.

7. The process of claim 1, further comprising regulating the flow of the oxygen-containing gas, the $C_2$-$C_6$ alkane, and the effluent by using poppet valves.

8. The process of claim 1, further comprising adding recycled flue gas from the RFR to the oxygen-containing gas prior to contacting the oxygen-containing gas with the oxygen transfer agent.

9. The process of claim 1, further comprising adding steam to the oxygen-containing gas prior to contacting the oxygen-containing gas with the oxygen transfer agent.

10. The process of claim 1, further comprising extracting heat from the $C_2$ to $C_6$ olefin to form high-pressure steam.

11. The process of claim 1, further comprising packing the oxygen transfer agent in the reactor in the form of pellets.

12. The process of claim 1, wherein the oxygen transfer agent is washcoated on a ceramic monolith.

13. The process of claim 1, wherein the oxygen transfer agent further comprises sodium.

14. The process of claim 1, wherein no fuel is burned to provide heat to the reactor.

15. The process of claim 1, wherein the oxygen transfer agent does not have a perovskite structure.

16. A process for oxydehydrogenation of a $C_2$ to $C_6$ alkane to a $C_2$ to $C_6$ olefin, comprising:
adding an oxygen-containing gas to a reactor;
contacting the oxygen-containing gas with an oxygen transfer agent comprising manganese, and tungsten to heat the reactor;
terminating the oxygen-containing gas flow;
adding a stream comprising $C_2$ to $C_6$ alkane to the reactor;
oxidatively dehydrogenating the stream by reacting the oxygen from the oxygen transfer agent with the $C_2$ to $C_6$ alkane to form $C_2$ to $C_6$ olefin and steam; and
withdrawing an effluent comprising the $C_2$ to $C_6$ olefin from the reactor, wherein the reactor is a reverse flow reactor.

17. The process of claim 16, further comprising purging the oxygen-containing gas from the reactor using steam, an inert gas, or a vacuum purge.

18. The process of claim 16, further comprising purging the $C_2$ to $C_6$ alkane and olefin from the reactor using steam, an inert gas, or a vacuum purge.

19. The process of claim 16, wherein the oxygen transfer agent comprises less than 1 wt. % of lithium, sodium, and potassium.

20. The process of claim 16, wherein th eoxygen transfer agen comprises from 0.5-2.0 moles of manganese and from 0.5-2.0 moles of at least one material selected from the group consiting of aluminum, cobalt, zirconium, yttrium, cerium, lanthanum, sodium, tungsten, and the oxides thereof.

21. The process of claim 16, where the oxygen transfer agent comprises cobalt, tin, and zirconium.

22. The process of claim 16, wherein the oxygen transfer agent further comprises sodium.

* * * * *